(12) United States Patent
Bradway et al.

(10) Patent No.: US 10,603,198 B2
(45) Date of Patent: Mar. 31, 2020

(54) PROSTHESIS DEPLOYMENT SYSTEM AND METHOD

(71) Applicant: Cook Medical Technologies LLC, Bloomington, IN (US)

(72) Inventors: Ryan C. Bradway, West Lafayette, IN (US); Kevin D. Wilger, Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 275 days.

(21) Appl. No.: 15/695,382

(22) Filed: Sep. 5, 2017

(65) Prior Publication Data

US 2018/0071125 A1    Mar. 15, 2018

Related U.S. Application Data

(60) Provisional application No. 62/385,593, filed on Sep. 9, 2016.

(51) Int. Cl.
*A61F 2/966* (2013.01)
*A61F 2/915* (2013.01)
(Continued)

(52) U.S. Cl.
CPC ............... *A61F 2/966* (2013.01); *A61F 2/07* (2013.01); *A61F 2/915* (2013.01);
(Continued)

(58) Field of Classification Search
CPC .. A61F 2/95; A61F 2/954; A61F 2/958; A61F 2/962; A61F 2/966; A61F 2/97;
(Continued)

(56) References Cited

U.S. PATENT DOCUMENTS 6,183,481 B1 * 2/2001 Lee .................. A61F 2/954
606/108
6,695,875 B2    2/2004 Stelter et al.
(Continued)

FOREIGN PATENT DOCUMENTS

| EP | 2870947 A1 | 5/2015 |
|---|---|---|
| WO | WO 2011/084342 A1 | 7/2011 |
| WO | WO 2015/010963 A1 | 1/2015 |

OTHER PUBLICATIONS

Extended European Search Report for corresponding EP 17275140 dated Jan. 16, 2018, 6 pages.

*Primary Examiner* — Katherine H Schwiker
(74) *Attorney, Agent, or Firm* — Brinks Gilson & Lione (57) ABSTRACT

The present embodiments provide a prosthesis deployment system, and method of deployment of a prosthesis using the same, having a positioning member at least partially disposed within a tubular segment of a tip assembly. The positioning member is movable between nondeployed and deployed configurations. In the nondeployed configuration the positioning member can permit the tip assembly to move relative to the enlarged body assembly. When an enlarged body is at a position farther away from a tip body, which may be at the edge of the tubular segment, the positioning member can move or flare to its deployed configuration to inhibit the enlarged body from moving relatively closer to the tip assembly. Axial force applied to the tip assembly during withdrawal of the tip assembly can be transmitted via the positioning member to the enlarged body assembly to facilitate its withdrawal from the body.

20 Claims, 6 Drawing Sheets

(51) Int. Cl.
*A61F 2/95* (2013.01)
*A61F 2/07* (2013.01)
*A61M 25/00* (2006.01)

(52) U.S. Cl.
CPC .............. *A61F 2002/9511* (2013.01); *A61F 2002/9517* (2013.01); *A61F 2002/9665* (2013.01); *A61F 2210/0014* (2013.01); *A61M 25/0074* (2013.01)

(58) Field of Classification Search
CPC .......... A61F 2/07; A61F 2/2427; A61F 2/243; A61F 2/2433; A61F 2/2436; A61F 2/2439; A61F 2002/9665; A61F 2002/9511; A61F 2002/9505; A61F 2002/9517; A61F 2002/9528; A61F 2002/9534; A61F 2002/011; A61B 2017/1205; A61B 2017/2054; A61B 2017/12059; A61B 2017/12063; A61B 2017/12068; A61B 2017/12072; A61B 2017/12077; A61B 2017/12081; A61B 2017/12086; A61B 2017/1209; A61B 2017/12095
See application file for complete search history.

(56) References Cited

U.S. PATENT DOCUMENTS

| | | | |
|---|---|---|---|
| 7,335,224 B2 | 2/2008 | Öhlenschlaeger | |
| 7,435,253 B1* | 10/2008 | Hartley | A61F 2/07 623/1.11 |
| 7,993,384 B2 | 8/2011 | Wu et al. | |
| 8,753,385 B2 | 6/2014 | Hartley et al. | |
| 8,808,346 B2 | 8/2014 | Jimenez, Jr. et al. | |
| 8,876,879 B2 | 11/2014 | Hartley et al. | |
| 8,888,834 B2 | 11/2014 | Hansen et al. | |
| 8,968,380 B2 | 3/2015 | Nimgaard | |
| 8,998,970 B2 | 4/2015 | Arbefeuille et al. | |
| 9,017,393 B2 | 4/2015 | Farag | |
| 2003/0225446 A1* | 12/2003 | Hartley | A61F 2/95 623/1.11 |
| 2007/0021820 A1* | 1/2007 | Sisken | A61F 2/958 623/1.11 |
| 2007/0219617 A1 | 9/2007 | Saint | |
| 2009/0105801 A1* | 4/2009 | Ivancev | A61F 2/966 623/1.11 |
| 2010/0234932 A1* | 9/2010 | Arbefeuille | A61F 2/95 623/1.11 |
| 2010/0274187 A1* | 10/2010 | Argentine | A61F 2/95 604/96.01 |
| 2011/0144735 A1* | 6/2011 | Hartley | A61F 2/95 623/1.11 |
| 2011/0295361 A1* | 12/2011 | Claiborne, III | A61F 2/2412 623/1.26 |
| 2012/0185031 A1 | 7/2012 | Ryan et al. | |
| 2012/0221093 A1 | 8/2012 | McHugo | |
| 2014/0046429 A1 | 2/2014 | Cragg et al. | |
| 2014/0180386 A1 | 6/2014 | Huser | |
| 2014/0257454 A1 | 9/2014 | McGee | |
| 2014/0277345 A1 | 9/2014 | Havel et al. | |
| 2015/0142097 A1* | 5/2015 | Coverdale | A61F 2/95 623/1.12 |
| 2015/0216694 A1 | 8/2015 | Ducke et al. | |
| 2017/0056169 A1* | 3/2017 | Johnson | A61F 2/2418 |
| 2017/0056219 A1 | 3/2017 | Bradway et al. | |
| 2017/0056220 A1 | 3/2017 | Bradway et al. | |
| 2017/0056222 A1 | 3/2017 | Bradway et al. | |
| 2017/0056224 A1 | 3/2017 | Baxter et al. | |
| 2017/0056225 A1 | 3/2017 | Baxter et al. | |

* cited by examiner

PROSTHESIS DEPLOYMENT SYSTEM AND METHOD

RELATED APPLICATIONS

This application claims the benefit of the filing date under 35 U.S.C. § 119(e) of Provisional U.S. Patent Application Ser. No. 62/385,593, filed Sep. 9, 2016, which is incorporated by reference in its entirety.

BACKGROUND

The present disclosure relates generally to medical devices, and more particularly, to a system and method for placement and deployment of a prosthesis in a vessel lumen.

The use of delivery devices or introducers employing catheters has long been known for a variety of medical procedures, including procedures for establishing, re-establishing or maintaining passages, cavities or lumens in vessels, organs or ducts in human and veterinary patients, occlusion of such vessels, delivering medical treatments, and other interventions. For these procedures, it has also long been known to deliver an implantable prosthesis by means of a catheter, often intraluminally. For example, a stent, stent-graft, vena cava filter, occlusion device, or other prostheses can be delivered intraluminally from the femoral artery, via a transapical approach and/or using other acceptable delivery locations and methods for deployment of the prosthesis.

For procedures in which a prosthesis or other medical device is implanted into a patient, the prosthesis to be implanted is normally held on a carrier catheter or cannula of the introducer in a compressed state. The prosthesis is positioned between the walls of the introducer and a sheath over the prosthesis. The prosthesis is then released from the cannula so as to expand to its normal operating state, prior to withdrawal of the cannula from the patient. In many devices, the steps to carry out the implantation can occur, for example, first by retracting a retractable sheath to expand or partially expand the prosthesis, and then performing further steps to, for example, release one or both ends of the prosthesis, deploy an anchoring stent, or the like. Other steps may include pushing a tubular shell of a dilator tip forward relative to a reverse tapered body in order to partially expand a top portion, such as a bare top stent, of the prosthesis. Often these steps require the physician operator to manipulate multiple handles and pin vises to lock and unlock relevant components. The prosthesis which is to be implanted within a patient's vessels by the delivery device may vary depending on various factors including the procedure being performed and the portion of the vessels being treated. The delivery device described herein can be configured to deploy a wide range of different prostheses including, but not limited to cuffs, single lumen tubular stent grafts, bifurcated AAA stent grafts, branched or fenestrated stent grafts and combinations thereof. In addition to facilitating the delivery of a wide range of prostheses, the delivery device can be used for a variety of delivery approaches to be utilized, including but not limited to transapical or femoral approaches.

SUMMARY

In one embodiment, a prosthesis deployment system is provided having a positioning member in a deployed configuration for inhibiting a tip body segment from moving relative to an enlarged body. The tip body segment is coupled to an end of an inner cannula. A tubular segment extends away from the tip body segment, defining a lumen between an internal axial end of the tip body segment and an edge of the tubular segment. The enlarged body is slidably disposed within the lumen of the tubular segment. The enlarged body is coupled to an end of a concentric cannula that is coaxially disposed about the inner cannula. The positioning member is at least partially disposed within the lumen of the tubular segment. The positioning member has a first member end coupled to one of the enlarged body or the tip body segment. The positioning member is deployable when the enlarged body is at a position corresponding to the edge of the tubular segment.

In one embodiment, a delivery device includes a flareable wire member having a member end coupled to an enlarged body member and extending toward the tip body segment. The system includes a tip cannula and a tip body segment coupled to an end of the tip cannula. A tubular segment is extended away from the tip body segment. The tubular segment defines a lumen extending through an end opening of the tubular segment and terminating at an internal end of the tip body segment. The device further includes an enlarged body cannula slidably disposed about the tip cannula. The enlarged body member is coupled to an end of the enlarged body cannula, and slidably disposed along the lumen of the tubular segment. The flareable wire member is radially movable about the member end between a nondeployed configuration and a deployed configuration. In its nondeployed configuration, at least a portion of the flareable wire member is received in a port formed in the tip body segment. In its deployed configuration, the flareable wire member is at least partially withdrawn from the port and moved radially within the tubular segment.

In another embodiment, a method of deployment of a prosthesis with a delivery device is provided. The method includes providing the delivery device that includes a tip assembly coupled to an end of an inner cannula. The tip assembly includes a tip body segment and a tubular segment extending from the tip body segment. The tubular segment defines a lumen extending through an end opening of the tubular segment and terminating at an internal axial end of the tip body segment. The lumen of the tubular segment receives a portion of a prosthesis in a radially compressed configuration. The system further includes an enlarged body coupled to a concentric cannula slidably disposed about the inner cannula, and a positioning member at least partially disposed within the tubular segment of the tip assembly at a nondeployed configuration. A step of the method includes moving relatively the enlarged body and the tip assembly by a distance for removing the tubular segment of the tip assembly from around a portion of the prosthesis to allow the portion of the prosthesis to radially expand. Another step of the method includes radially moving the positioning member within the tubular segment from its nondeployed configuration to a deployed configuration, the positioning member in its deployed configuration inhibiting the tip assembly from moving relatively closer to the enlarged body after the relative movement between the enlarged body and the tip assembly by the distance.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

In the present application, the term "proximal" when referring to a delivery device refers to a direction that is farthest away from an operator using a delivery device, while the term "distal" refers to a direction that is generally closest to the operator using the delivery device. The proximal and distal ends of a delivery device may also be referred to as an introduction end of the delivery device and an operator end of the delivery device, respectively. The term "operator end" of the delivery device is that portion of the device that is intended to remain outside of a patient during a procedure. The term "introduction end" of the delivery device, which is opposite to the operator end, is that portion of the device that is intended to be inserted within a patient during a procedure. When referring to the prosthesis itself relative to the delivery device, the proximal end of the prosthesis is that part of the prosthesis closest in proximity to the introduction end of the delivery device and the distal end of the prosthesis is that end that is closest in proximity to the operator end of the delivery device. When referring to the prosthesis relative to placement in the human body of the patient, the ends of the various devices and parts of devices may be referred to as the inflow end (that end that receives fluid first, and the outflow end (that end from which the fluid exits).

Figure 1:
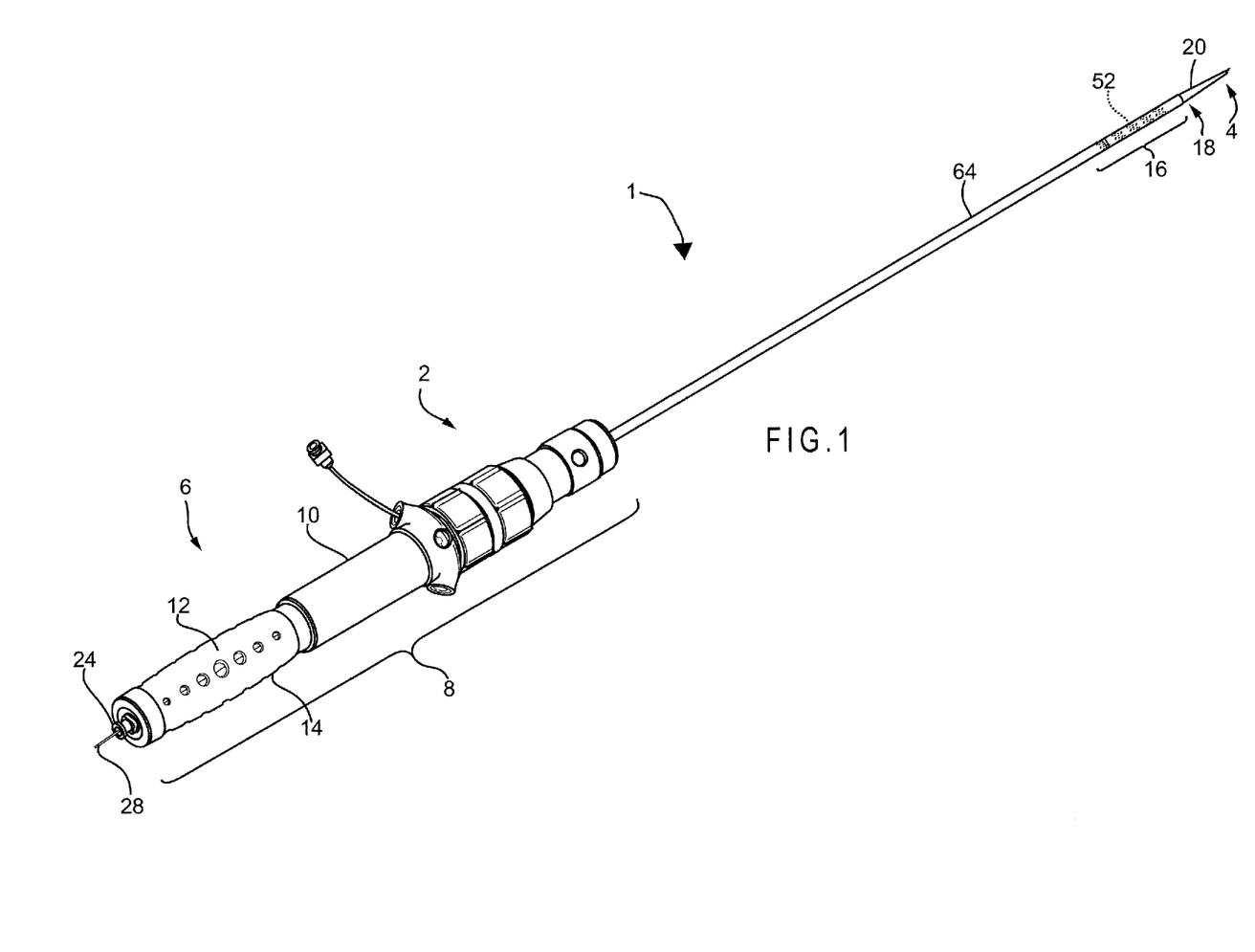
FIG. 1 is a perspective view of an example of a prosthesis deployment system having a prosthesis in a radially compressed configuration.

Referring initially to FIG. 1, a prosthesis deployment system 1 is provided to include a delivery device 2 and a prosthesis 52 loaded in the delivery device 2. An example of the delivery device 2 includes a proximal or introduction end 4 and a distal operator end 6. A handle assembly 8 is located adjacent the distal operator end 6 of the device 2. In one example, the handle assembly 8 may include a first or main handle 10. This may be the front most handle that is closest in proximity to the introduction end 4 of the delivery device 2. The handle assembly 8 may further include additional handles, such as, for example, a second or intermediate handle 12 and a third or rearmost handle 14 that is closest in proximity to the distal operator end 6. The main handle 10 can be fixed relative to the delivery device 2. In one example, the main handle 10 may also be fixed relative to the intermediate handle 12 and/or to the rearmost handle 14, with the intermediate handle 12 and the rearmost handle 14 being separately and independently rotatable relative to the main handle 10 and to each other. Further details of examples of a handle assembly that can be used to manipulate the prosthesis deployment are described herein and in U.S. Provisional Application No. 62/212,767 filed on Sep. 1, 2015, which application is incorporated by reference herein in its entirety. Other handle assemblies that are manipulated through liner displacement may also be used.

As shown in FIG. 1, the introduction end 4 of the delivery device 2 includes a retention region 16 upon which the prosthesis 52 can be releasably coupled and a tip assembly or nose cone dilator 18. The tip assembly 18 may include a proximal tip body segment 20 and a tubular segment 21 (also known as a top cap and shown in FIGS. 2-7) extending away from the tip body segment 20 toward the operator end 6 of the delivery device 2.

Figure 8:
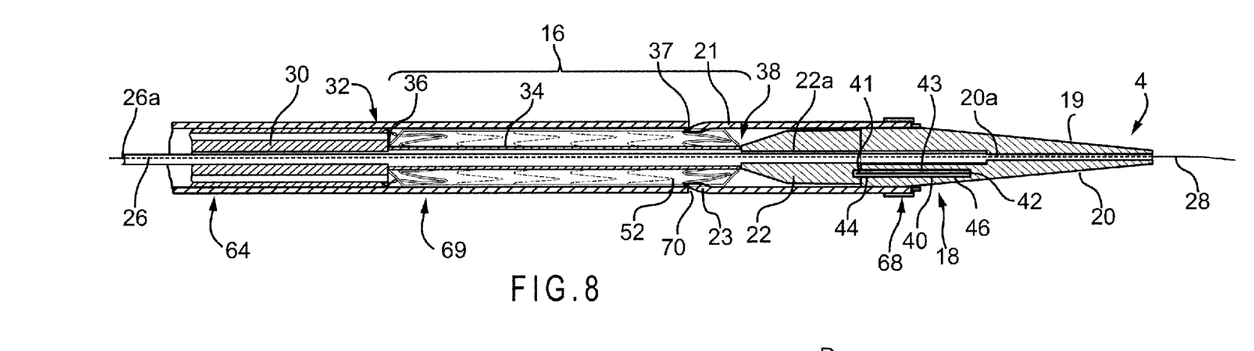
FIG. 8 is a cross-sectional view of a proximal end of the prosthesis deployment system of FIG. 1, with an outer sheath in an extended position, a prosthesis in a radially compressed configuration, and an example of a positioning member in a nondeployed configuration.
Figures 9, 10:
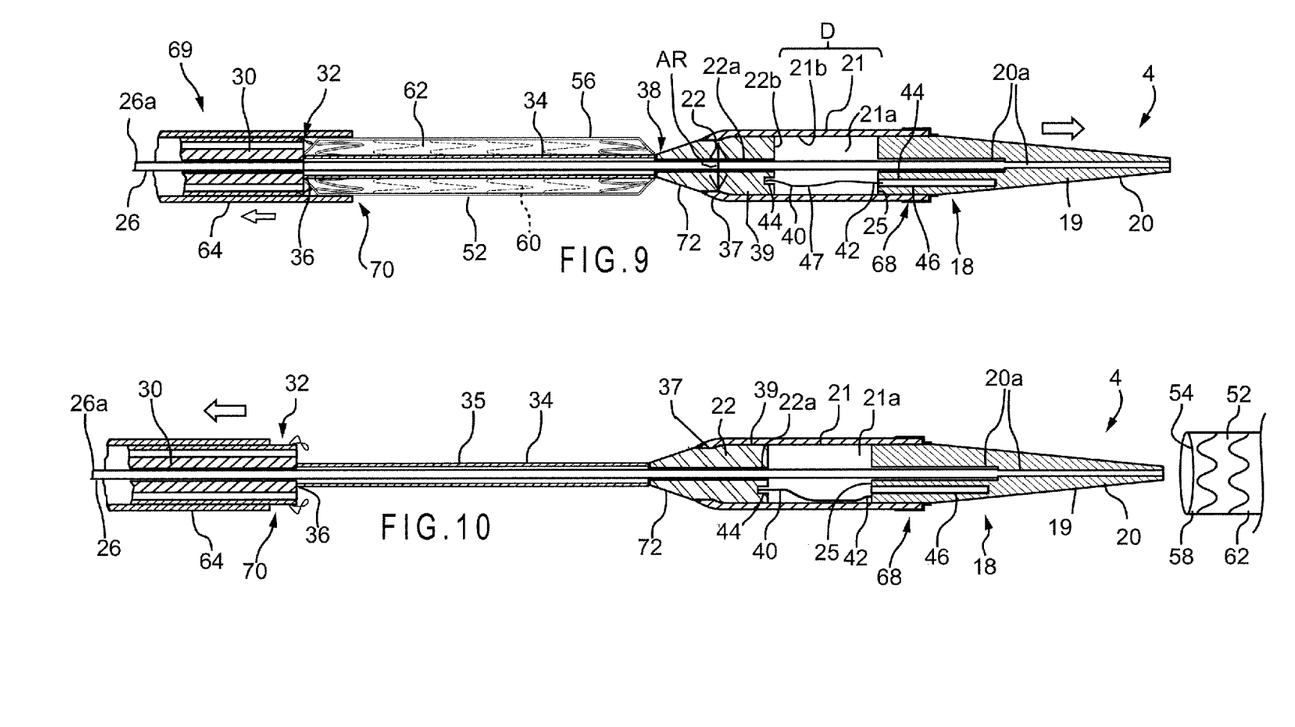
FIG. 9 is a cross-sectional view of a proximal end of the prosthesis deployment system of FIG. 1, with an outer sheath partially retracted distally and a tip assembly moved fully away from a prosthesis with a portion thereof being radially expanded, and an example of a positioning member in a deployed configuration.
FIG. 10 is a cross-sectional view of a proximal end of the prosthesis deployment system of FIG. 1, with a delivery device being withdrawn distally from a lumen of a prosthesis in a radially expanded configuration.

As shown further in FIGS. 8-10, the tip body segment 20 can be shaped to include a forward proximal taper 19 and include an inner lumen 20a extending therethrough to receive a guide wire 28 (shown FIG. 8). Further in FIG. 9, an internal wall 21b of the tubular segment 21 defines a segment lumen 21a. The segment lumen 21a may extend between an end opening 23 defined at the distal end of the tubular segment 21 and terminating at an internal axial end 25 at the distal end of the tip body segment 20.

Also shown in FIGS. 8-10, a separate distal enlarged body 22 may be disposed adjacent to the tip assembly 18. The enlarged body 22 may be shaped to have a reverse distal taper 72 and include an inner lumen 22a formed axially therein. The tip assembly 18 may present a smooth tapered surface to facilitate entry into and movement through a body vessel and facilitate deployment of the prostheses 52, as will be described in further detail below. Tip assembly 18 may include radiopaque material or be equipped with a radiopaque marker (not shown) to facilitate visualization of the tip assembly 18 in use provided by desired imaging modality (i.e., by fluoroscopy, MRI, 3D or other imaging techniques).

As shown in FIG. 1, an inner cannula 26 extends the longitudinal length of the delivery device 2, from the distal operator end 6 of the device 2 to the tip body segment 20 at the introduction end 4 of the device 2. A pin vise 24 is shown provided along the handle assembly 8 and used to selectively lock the inner cannula 26, as can be appreciated by those of ordinary skill. The inner cannula 26 can be connected at one end (its distal end) within the handle assembly 8 in a manner to facilitate pushing the inner cannula forward or proximally and pulling the inner cannula backwardly relative to the delivery device 2, as described further herein. At its other end (its proximal end), the inner cannula 26 may be moveably received within the inner lumen 22a of the enlarged body 22, as shown in FIGS. 8-10, and can be fixedly attached within the inner lumen 20a of the tip body segment 20 to define another aspect of the tip assembly 18. More particularly, the inner cannula 26 extends through the inner lumen 22a of the enlarged body 22, which can be configured to allow the inner cannula 26 to move or slide longitudinally therein.

The inner cannula 26 also extends through the inner lumen 20a of the tip body segment 20, and can be attached or coupled to the tip body segment 20 by various means, including adhesives, welding, and/or other suitable attachment mechanism. In one example, the inner cannula 26 can be attached to the tip body segment 20 by an overmolding process and a gluing process. As a result, pushing movement of the inner cannula 26 in a forward (proximal) direction simultaneously causes forward (proximal) longitudinal movement of the inner cannula 26 as well as forward (proximal) movement of the tip body segment 20 of the tip assembly 18.

In an example, the inner cannula 26, the tip body segment 20, and the tubular segment 21 may define an integral unit of the tip assembly 18, moving together when force is applied to either one. The inner cannula 26 includes an inner lumen 26a to accommodate the guide wire 28, as shown in FIG. 8, for tracking the delivery device 2 to a desired position within a patient's vasculature and which can also be used for flushing or injection of fluids. The inner cannula 26 can be made of a variety of suitable materials that are stiff, yet flexible enough to allow the inner cannula 26 to conform to the tortious anatomy of a patient during use, and can be either straight or have a curve imparted to a portion of it.

With reference to FIGS. 2-10, a pusher 30, sometimes also referred to as a positioner or stiffening cannula, can be disposed coaxially over at least a portion of the inner cannula 26. The pusher 30 can be a cannula constructed from various materials, and in one example, a proximal portion of the pusher which is introduced into the patient can comprise a polymer, sometimes referred to as VRDT (or vinyl radiopaque dilator tubing), plastics, metals, alloys or a combination thereof, whereas a distal portion of the pusher 30 can comprise the same material as the proximal portion of the pusher 30 or it can be a different material including but not limited to plastics, polymers, alloys, metals or a combination thereof, that provide sufficient maneuverability and stiffness to the pusher 30 as necessary and desired. The pusher 30 can extend from a location just back of the prosthesis retention region 16 coaxial with a length of the inner cannula 26 and terminate at an operator end within the handle assembly 8. In one example, the distal end of the pusher 30 (closest to the distal operator end 6 of the delivery device 2) can be directly or indirectly attached to the main handle 10 by various means, including threaded attachment, adhesives, welding, and/or other suitable attachment mechanisms. For a length of the pusher 30, a stiffening rod (not shown) can be disposed over the inner cannula 26 and/or over the pusher 30 for additional stability and maneuverability.

As shown in FIGS. 7-10, a concentric cannula 34 can be disposed coaxially over a portion of the inner cannula 26 at the prosthesis retention region 16. A distal end 36 of the concentric cannula 34 (closest to the operator end of the delivery device 2) can be attached or coupled to the front (proximal) end 32 of, or in some examples coextension with, the pusher 30 by various means, including adhesives, welding, and/or other suitable attachment mechanisms. A proximal end 38 of the concentric cannula 34 (opposite the distal end 36) can be attached or coupled to the enlarged body 22 by various means, including adhesives, welding, and/or other suitable attachment mechanisms such that the pusher 30, the concentric cannula 34 and the enlarged body 22 together define an enlarged body assembly 35. In other words, the elements extend substantially in tandem in a direction from the distal operator end 6 toward the introduction end 4 of the delivery device 2: pusher front end-concentric cannula backend-concentric cannula front end-enlarged body.

In an example, the pusher 30, the concentric cannula 34, and the enlarged body 22 defines an integral unit of the enlarged body assembly 35, moving together when force is applied to any one of them. The concentric cannula 34 can be constructed from various materials including but not limited to plastics, polymers, alloys, metals or a combination thereof, that provide sufficient maneuverability and stiffness to the concentric cannula 34 as necessary and desired. In one example, concentric cannula 34 can be constructed of a flexible, high-tensile polymeric material such as polyetheretherketone (PEEK).

A positioning member 40 is shown extending at least partially disposed within the segment lumen 21a of the tubular segment 21 of the tip assembly 18. As will be described, the positioning member 40 when deployed can fix or lock the relative position between the enlarged body 22 and the tip assembly 18 in a manner such that any axial force transmitted via the inner cannula 26 and the tip assembly 18 can be now transferred to the enlarged body 22 and the concentric cannula 34, and vice versa, during movement and withdrawal of the delivery device 2. The positioning member 40 may be movable from a nondeployed configuration to a deployed configuration. The positioning member 40 can be generally maintained in the nondeployed configuration, shown, for example, in FIGS. 2 and 8 when the enlarged body 22 is at a first position in close proximity to the internal axial end 25 of the tip body segment 20 of the tip assembly 18. This can occur when the enlarged body 22 is disposed adjacent and/or in abutment with the internal axial end 25 of the tip body segment 20, which can include when the tip body segment 20 is advanced proximally away from the enlarged body 22 by an initial distance. In the nondeployed configuration, the positioning member 40 still permits the tip assembly 18 to move axially in either proximal or distal direction relative to the enlarged body 22. For example, the tip assembly 18 can be moved distally and/or proximally with respect to the enlarged body assembly 35. The positioning member 40 described herein can be a wire member or a tubular member constructed of polymers, metals and/or alloys, including nitinol or stainless steel. For example, FIG. 8 shows the positioning member 40 in the nondeployed configuration being disposed in a receiving channel 46, as will be further defined.

The positioning member 40 can be moved to the deployed configuration, shown, for example, in FIGS. 4-7 and 9-10, when the enlarged body 22 is no longer in close proximity to the internal axial end 25 of the tip body segment 20 of the tip assembly 18. In this configuration, the positioning member 40 extends out of or is removed from the receiving channel 46. This can occur when the tip body segment 20 is advanced proximally away from the enlarged body 22 beyond an initial distance, and in some instances, a predetermined distance D to a second position, to allow the positioning member 40 to deploy. During deployment, the positioning member may move within the segment lumen 21a in the radial direction, axial direction, the lateral direction, or in any combination thereof. To this end, after being moved the predetermined distance D, the positioning member 40 moves to a position within the segment lumen 21a in between the tip body segment 20 and the enlarged body 22 that inhibits the tip assembly 18 from moving axially relatively closer to the enlarged body 22 and helps fix the position of the enlarged body 22 at a distal end 37 of the tubular segment 21 (the end closest to the distal operator end 6 of the delivery device 2). The annular space defined by the internal wall 21b of the tubular segment 21 and the inner cannula 26 can be sized to physically constrain or confine the positioning member 40 from further compressive movement. To this end, when a compressive axial force is applied to the positioning member 40 between the enlarged body 22 and the tip body segment 20, the positioning member 40 may bow along a single point (as shown in FIG. 10) or multiple points outwardly to engage the internal wall 21b and/or inwardly to engage the inner cannula 26, which further stiffens the positioning member 40 in the axial direction. For example, the tip assembly 18 can be prevented from being moved distally with respect to the enlarged body assembly 35, and the enlarged body assembly 35 can be prevented from being moved proximally with respect to the tip assembly 18, and vice versa.

In one example, the positioning member 40 may be maintained within the segment lumen 21a of the tubular segment 21 during its movement between the nondeployed and deployed configurations. The tubular segment 21 can guard or protect the prosthesis 52 from interaction with the positioning member 40 during the deployment of the prosthesis and removal of the device 2 from the body. The tubular segment 21 of the tip assembly 18 and the enlarged body 22 can be configured to inhibit further relative movement between them beyond the predetermined distance D during deployment. In one example, with reference to FIGS. 9-10, the distal end 37 of the tubular segment 21 may be shaped with an internal tapered portion to define an opening with a reduced cross-sectional area AR compared to the general cross-sectional area of the remaining segment lumen 21a. In this regard, the enlarged body 22 may include a cylindrical proximal end 39 sized to slide within the segment lumen 21a, and sized greater than the reduced cross-sectional area of the tapered distal end 37. To this end, the tapered distal end 37 upon engagement with the proximal end 39 of the enlarged body 22 inhibits further relative movement away from the tip assembly 18.

In one example, when the tip body segment 20 is advanced proximally away from the enlarged body 22 at the predetermined distance D, the tip assembly 18 can be inhibited from moving any farther away from the enlarged body 22 and out of the tubular segment lumen 21a by the engagement of the tapered distal end 37 and the proximal end 39 of the enlarged body 22. Also, during such engagement the deployment of the positioning member 40 can occur, and the tip assembly 18 can be inhibited from moving any closer to the enlarged body 22. To this end, the relative position of the enlarged body 22 and the tip assembly 18 can be fixed or locked and directly coupled with the positioning member 40, such that any axial force transmitted via the inner cannula 26 and the tip assembly 18 can be now transferred to the enlarged body 22 and the concentric cannula 34, and vice versa.

The positioning member 40 can include a first member end 41, shown, for example, in FIG. 8, coupled to one of the enlarged body 22 or the tip body segment 20. The positioning member 40 can include a member body 43 extending between the first member end 41 and a second member end 42, disposed opposite to the first member end 41. The second member end 42 can be a free end engageable with the other of the enlarged body 22 or the tip body segment 20. In one example, the first member end 41 is a fixed end, while the second member end 42 is a free, movable end. In FIGS. 8-10 the first member end 41 is shown coupled to the enlarged body 22, while the second member end 42 is engageable with the tip body segment 20.

In one example, the first member end 41 of the positioning member 40 can be fixedly coupled to the enlarged body 22. For example, as shown in FIGS. 8-10, a coupling port 44 can be formed in the proximally facing axial end 22b of the enlarged body 22. The coupling port 44 can be sized and shaped to receive the first member end 41 and coupled to the positioning member 40 with an adhesive, welding, or other attachment means. The second member end 42 of the positioning member 40 is shown movably received within the receiving lumen or channel 46 formed in the tip assembly 18, and particularly, within the tip body segment 20, as shown in FIGS. 9-10. To this end, when the tip body segment 20 is advanced proximally away from the enlarged body 22 by the predetermined distance D, for example, in the direction of the arrow away from the operator, to deploy the positioning member, the positioning member 40 can be moved at least partially from the receiving channel 46 and the second member end 42 moves in the radial and/or lateral direction away from the entry to the receiving channel 46 to engage the surface of the internal axial end 25 of the tip body segment 20 as shown in FIG. 10. In one example, the second member end 42 engages a target zone of the internal axial end 25 of the tip body segment 20 outside the entrance of the receiving channel 46. As will be described, other portions of the tip assembly 18 or the enlarged body 22 can perform as a physical stop and engage the second member end 42.

The receiving channel 46 can be sized and shaped to receive substantially the entire positioning member body 43, that is, the second member end 42 and the body 43 except what is coupled to the enlarged body 22. Though the receiving channel 46 is shown to be shaped linearly and axially aligned with the inner lumen 20a of the tip body segment 20, the receiving channel 46 can have other configurations, such as, for example and not limited to, being shaped linearly and obliquely angled with the respect to the inner lumen 20a, being shape irregularly or even shaped coiled around the inner lumen 20a.

The positioning member 40 may have a spring bias, moving or flaring radially and/or laterally outward or inward under a spring force from its first position in the nondeployed configuration to its biased second position in the deployed configuration. To this end, the positioning member 40 can be configured to bias the body 43 of the positioning member 40 and its second member end 42 to its second position at the target zone, such that when placed in its first position or any other position, the positioning member 40 will automatically return to its biased second position. In one example, the positioning member 40 includes an undulation or a bend 47 along its body 43 to facilitate the biasing of the positioning member, as shown in FIG. 9.

Figure 11A:
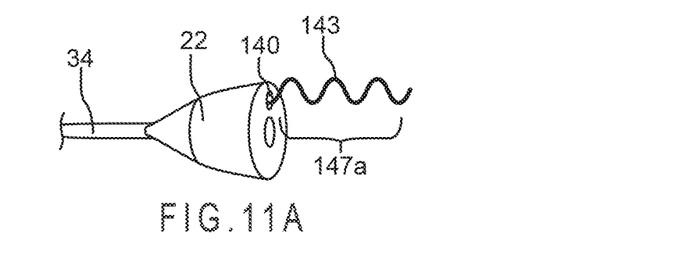
FIG. 11A is a partial view of an enlarged body coupled to a concentric cannula, having an example of a positioning member having a series of undulations.

The positioning member 40 can include a series of undulations or bends along its body such as shown in FIG. 11A. For example, in FIG. 11A, the positioning member 140 shown extending from the enlarged body 22 coupled to the concentric cannula 34 includes a series of undulations or bends 147a along its body 143 to define a spring-like wire structure or a coiled ribbon structure. The positioning member 140 may be capable of being at least partially straightened to be received in the receiving channel (not shown), and expanded to its undulated configuration once removed from the receiving channel. The annular space defined by the internal wall 21b of the tubular segment 21 and the inner cannula 26 can be sized to physically constrain or confine the undulated positioning member. To this end, when a compressive axial force is applied to the undulated positioning member, the element forming the undulations will engage the internal walls 21b, which confine the undulated positioning member from axially moving any further. When this occurs, the positioning member body 143 performs like an axial member.

Figure 11B:
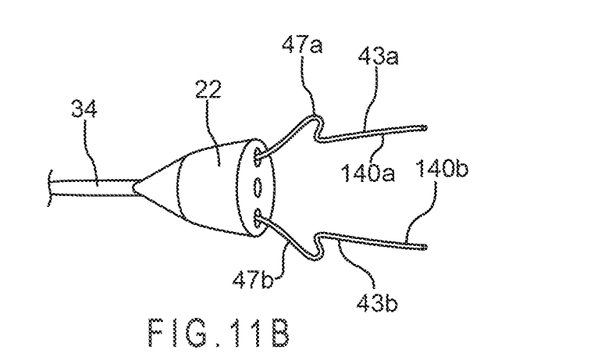
FIG. 11B is a partial view of an enlarged body coupled to a concentric cannula, having an example of a pair of positioning members.
Figure 11C:
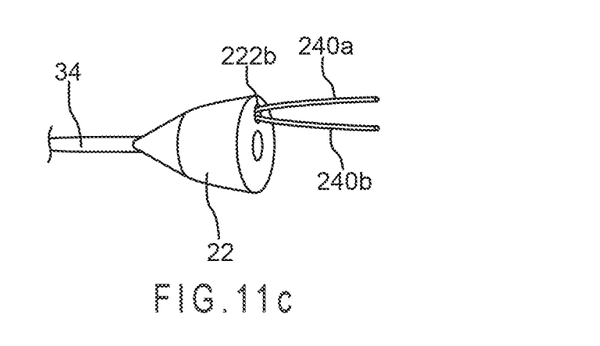
FIG. 11C is a partial view of an enlarged body coupled to a concentric cannula, having an example of a pair of positioning members extending from a same location.

More than one positioning member can be included. For example, in FIG. 11B, a first positioning member 140a and a second positioning member 140b are shown extending at a different location along the axial end of the enlarged body 22. A second receiving channel (not shown) would need to be included within the tip assembly to receive the second positioning member in a manner similar to what is described earlier. The positioning members 140a and 140b can include one or more undulations or bends 47a, 47b along their bodies 43a, 43b such as shown in FIG. 11B. In another example, in FIG. 11C, the first positioning member 240a and the second positioning member 240b are shown extending from the same location or coupling port from the axial end of the enlarged body 22. Here, the coupling port 222b formed in the enlarged body 22 can be size to receive both first member ends of the first and second positioning members 240a, 240b, respectively, or separate coupling ports (not shown) can be formed in close proximity to one another.

Figure 12A:
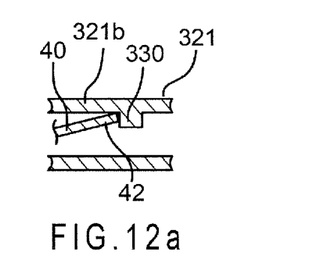
FIG. 12A is a partial cross-sectional view of an example of a tubular segment including a protruding tab for contacting an end of a positioning member.

In some instances, it can be desirable to place a physical stop element along the internal wall of the tubular segment 21 or an internal wall that defines the receiving channel 46. FIG. 12A depicts a partial cross section of another example of the tubular segment 321. A protruding radial tab 330 depending from the internal wall 321b of the tubular segment 321. When the tip assembly is advanced proximally relative to the enlarged body and the second member end 42 of the positioning member 40 passes the axial end of the tip body segment, the second member end 42 further travels within the tubular segment 321 until engaging the protruding radial tab 330. Although not shown, the protruding radial tab 330 can depend from the internal wall that defines the receiving channel in a similar manner. Here, the tip assembly 18 can be advanced proximally relative to the enlarged body 22 until the second member end 42 of the positioning member 40 engages such tab formed in the receiving channel without passing the axial end of the tip body segment.

Figure 12B:
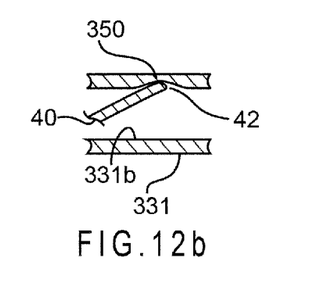
FIG. 12B is a partial cross-sectional view of an example of a tubular segment including a groove for contacting an end of a positioning member.

FIG. 12B depicts a partial cross section of another example of the tubular segment 331. A groove 350 formed into the internal wall 331b of the tubular segment 331. In this example, when the tip assembly 18 is advanced proximally relative to the enlarged body and the second member end 42 of the positioning member 40 passes the axial end of the tip body segment, the second member end 42 further travels within the tubular segment 321 until engaging the groove 350. In addition to, or separately, the groove 350 can be configured to capture an undulation formed in the positioning member.

Figure 13:
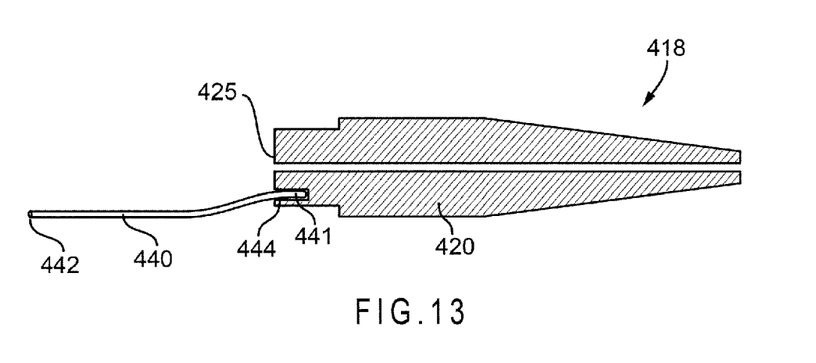
FIG. 13 is a cross-sectional view of a tip assembly and an example of a positioning member extending from the tip assembly.
Figure 14:
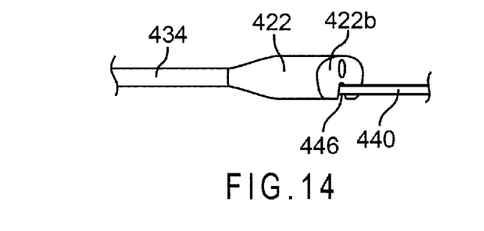
FIG. 14 is a perspective view of an example of an enlarged body coupled to a concentric cannula, having a receiving channel.

FIG. 13 depicts a partial cross-section of another example of the tip assembly 418. The positioning member 440 includes the first member end 441 fixed to the tip body segment 420 of the tip assembly 418, and the second member end 442 is a free end. The coupling port 444 can be formed into the internal end 425 of the tip body segment 420. In this example, as shown in FIG. 14, the enlarged body 422 coupled to the concentric cannula 434 includes the receiving channel 446 formed in the axial end 422b of the enlarged body 422. The receiving channel 446 can be various shapes such as the elongated shape shown previously, or a notched port formed in the outer surface 466 of the enlarged body 422 as shown in FIG. 14. The receiving channel 446 can be obliquely angled shaped extending between the face of the axial end 422b and the outer surface 466 of the enlarged body 422. The tip assembly 418 and the enlarged body 422 when brought together to move the positioning member 440 to its nondeployed configuration, the receiving channel 446 receives the positioning member 440 and a portion of the positioning member 440 can extend beyond the enlarged body 422 due to their relative sizes. To this end, when the tip body segment 420 is advanced proximally away from the enlarged body 422 to the predetermined distance to deploy the positioning member, the positioning member 440 can be moved at least partially from the receiving channel 446 and the second member end 442 can be moved in the radial direction to engage the axial end 422b of the enlarged body 422.

The delivery device 2 can be used to deliver and deploy a wide variety of prostheses, including variously sized and shaped stent grafts. FIG. 1 illustrates one exemplary prosthesis 52 in dashed lines to indicate that it is a generic prosthesis for illustrative purposes and that any one or more different prostheses can be interchanged and be releasably coupled to the delivery device 2 in a similar fashion. Several non-limiting examples of prostheses 52, which can be delivered to and deployed within a patient in a controlled and sequential manner using the delivery device 2, are described further herein.

As shown in FIGS. 2-10, the prosthesis 52, such as a stent graft, is carried on the delivery device 2 at the proximal end 4. More specifically, the prosthesis 52 can be carried on the concentric cannula 34 at the prosthesis retention region 16. In one example, the prosthesis 52 has an uncoupled state in which a tubular graft body 62 and expandable stents 60 of the prosthesis 52 are positioned coaxially over the inner cannula 26 and the concentric cannula 34 with a proximal or outflow end 56 of the prosthesis 52 in longitudinal proximity relative to the enlarged body 22. During assembly, a distal or inflow end 58 of the prosthesis 52 can be releasably coupled to the proximal end 32 of the pusher 30 and the proximal end 56 of the prosthesis 52 can be releasably coupled to the enlarged body 22 of the tip assembly 18, as described below.

The prosthesis 52 can be releasably coupled to the delivery device 2 at the prosthesis retention region 16 in a variety of ways. In one example, a prosthesis attachment mechanism releasably can couple the distal end 58 and/or the proximal end 56 of the prosthesis 52 to the proximal end 32 of the pusher 30. More particularly, the attachment mechanism can comprise one or more distal trigger wires 48 and one or more proximal trigger wires (not shown) each having a proximal end. However, other attachment mechanisms, including more trigger wires can also be used to releasably couple the distal end 58 and/or proximal end 56 of the prosthesis 52 to the pusher 30. Further, other attachment mechanisms, in addition to the distal and/or proximal trigger wires, can also be used to couple the distal end 58 and/or proximal end 56 of the prosthesis 52 to the delivery device 2, such as diameter reducing ties, a retractable sheath, sutures and the like as will be recognized by one of skill in the art. U.S. Patent App. Publication No. 2014/0180386, filed on Aug. 20, 2013, describes one example of a releasable diameter reducing tie, which application is incorporated by reference herein in its entirety.

The distal trigger wires 48 can extend longitudinally within a lumen of pusher 30 proximally from the handle assembly 8 to the respective distal end 58 of the prosthesis 52. The proximal ends of the distal trigger wires 48 exit the pusher 30 at its proximal end 32 and can be releasably coupled to the distal end 58 of the prosthesis 52. The proximal trigger wires can extend longitudinally within a lumen of the pusher 30 proximally from the handle assembly 8 and further within the lumen 54 of the prosthesis 52 to the proximal end 56 of the prosthesis 52. The proximal ends of the one or more proximal trigger wires exit the graft body to a portion of the tip assembly and can be releasably coupled to the proximal end 56 of the prosthesis 52. For example, the proximal ends of the one or more proximal trigger wires can be retained within the enlarged body 22, such as by friction fit, adhesives, or other suitable releasable attachment means so as to hold the proximal end 56 of the prosthesis 52 in a radially compressed delivery configuration and allow for the trigger wires to be pulled distally and released from the inner cannula 26 when deployment of the proximal end of the prosthesis 52 is necessary or desired. Other suitable attachment methods or mechanisms can be used to removably attach the proximal trigger wires to the proximal end of the prosthesis 52 as would be recognized by one of skill in the art.

More particularly, the distal ends of the distal trigger wires 48 and/or the proximal trigger wires can be coupled to one or more trigger wire release mechanisms that are disposed about and/or around at least a portion of the main handle 10. In one example, the distal trigger wires 48 and/or the proximal trigger wire can be directly or indirectly attached to the distal end 58 and the proximal end 56 of the prosthesis 52, respectively. For example, the distal and proximal trigger wires can engage suture loops (not shown) which are attached to the respective distal and proximal ends of the prosthesis 52. In this way, the trigger wires do not weave directly through the graft body 62. Alternatively, the trigger wires can be woven directly through or removably attached to the graft body 62 or woven over or through one or more of the stents 60 at the distal end 58 and proximal end 56 of the prosthesis 52. In the event that the prosthesis 52 includes a bare anchoring stent (not shown) extending proximally from the proximal end 56, the one or more trigger wires my weave over and/or through the proximal bare stent to releasably couple the proximal end 56 of the prosthesis to the enlarged body 22. Again, the prosthesis 52 is used for exemplary purposes only in this particular description of prosthesis attachment, but any type of prosthesis can be releasably coupled to the inner cannula in this manner. Other suitable attachment methods or mechanisms can be used to removably attach one or more distal and/or proximal trigger wires to the ends of the prosthesis 52, thereby coupling the prosthesis to the pusher 30 until the trigger wire(s) are released during deployment, as would be recognized by one of skill in the art.

When deployment is desired, distal retraction of the trigger wires (such as by manipulation of one or more trigger wire release mechanisms of the handle assembly 8) allows the proximal ends of the trigger wires to be released from the proximal and distal ends of the prosthesis 52, allowing the proximal and distal ends of the prosthesis 52 to at least partially deploy radially outwardly within a vessel. If other diameter reducing ties are being used to radially restrain the proximal and distal ends of the prosthesis 52, those ties can also be removed by manipulation of the trigger wire release mechanisms to allow the prosthesis to move from a radially inwardly constrained delivery configuration to a radially outwardly expanded configuration and fully deploy from delivery device 2 within the vessel.

The above description of the coupling of prosthesis 52 to the delivery device 2 is for exemplary purposes, and shall not be considered limiting, as different prostheses can be releasably coupled to the delivery device in different ways, and the proximal and distal ends of a particular prosthesis can be coupled to the delivery device in different ways. In addition, several other non-limiting examples of attachment and release mechanisms for the distal and proximal ends of the prosthesis 52 that can be operated and manipulated using the handle assembly 8 are described herein.

The releasable coupling of prosthesis 52 to the delivery device 2 at the prosthesis retention region 16 secures the prosthesis 52 to the delivery device 2 to radially inwardly restrain the prosthesis 52 in a manner that can subsequently facilitate insertion of the subassembly comprising the inner cannula 26, the pusher 30, the concentric cannula 34, and the prosthesis 52 into an outer sheath 64. As will be apparent, the outer sheath 64 in an extended position can be configured to radially restrain other regions of the prosthesis 52 for maintaining the prosthesis in a radially compressed, low-profile delivery configuration (see FIGS. 2 and 8) to a target site within a patient's anatomy. For deployment, the outer sheath 64 can be then retracted from the extended position to a more retracted position where the outer sheath 64 no longer radially restrains the prosthesis regions, thereby allowing for radial expansion of the prosthesis. As shown in FIGS. 1, 3-4, and 9-10, the outer sheath 64 can be longitudinally slideable and retractable and can be sized to extend along the length of the delivery device 2 from the intermediate handle 12 to the tip assembly 18. The outer sheath 64 can be disposed coaxially about and/or over at least a portion of the inner cannula 26 and the concentric cannula 34.

The tubular segment 21 of the tip assembly 18 can be disposed coaxially over a proximal portion of the inner cannula 26 and can be attached or otherwise secured at its proximal end 68 to the distal end of the tip body segment 20 (see FIGS. 8-10), for example at or about the point where the forward proximal taper of the tip body segment begins, such as by adhesives, bonding, welding or other suitable attachment mechanisms. The tubular segment 21 and the tip body segment 20 can be formed integrally as a unit. The tubular segment 21 can be indirectly attached to the inner cannula 26 via the tip body segment 20. As a result, pushing the inner cannula 26 in a proximal direction away from the distal operator end 6 of the delivery device 2 simultaneously causes proximal longitudinal movement of the inner cannula 26 as well as proximal movement of the tip body segment 20 and the tubular segment 21, and vice versa. A proximal end portion 69 of the outer sheath 64, in its extended position, can be disposed coaxially over at least a portion of the pusher 30, over a proximal portion of the inner cannula 26, and a proximal portion of the concentric cannula 34. The outer sheath 64 can be connected at its distal end within the handle assembly 8 to facilitate retraction of the outer sheath 64 distally.

In one example, a proximal end 70 of the outer sheath 64, in its extended position, can be generally aligned along at least a portion of the prosthesis 52 such that the proximal end portion 69 of the outer sheath 64 and a distal portion of the tubular segment 21 are disposed over adjacent segments of the prosthesis 52 in the radially compressed configuration. In one example, the proximal end 70 of the outer sheath 64 can be positioned adjacent to the distal end 37 of the tubular segment 21. In one example, the proximal end 70 of the outer sheath 64 can be disposed coaxially over a portion of the tubular segment 21.

Figure 2:
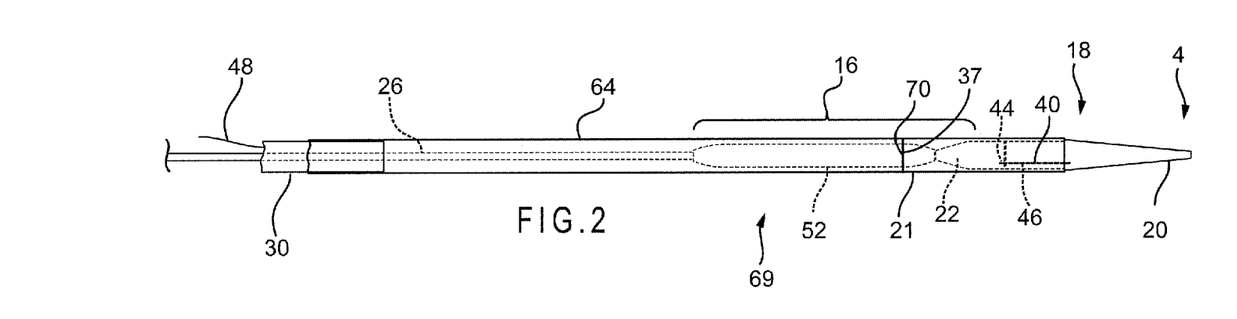
FIG. 2 is a side view of a proximal end of the prosthesis deployment system of FIG. 1, with an outer sheath in an extended position, a prosthesis in a radially compressed configuration, and an example of a positioning member in a nondeployed configuration.

As shown in FIGS. 2 and 8, before use of the delivery device 2 and during a procedure when the delivery device is tracked to a desired location within a patient's body, the prosthesis 52 disposed at the proximal or introduction end 4 of the delivery device 2 can be fully covered by a combination of the outer sheath 64 and the tubular segment 21 and held in its radially compressed, lowprofile delivery configuration. The positioning member 40 in its nondeployed configuration is shown residing within the receiving channel 46 formed in the tip body segment 20 of the tip assembly 18. To deploy the prosthesis 52 in a vessel lumen, removal of the tubular segment 21 and the proximal end portion 69 of the outer sheath 64 can proceed in two actions or manipulations of the handle assembly 8, separately or simultaneously.

In one example, a first action can be to push the tubular segment 21 in the proximal direction (shown by the arrow in FIGS. 3, 4 and 9) so as to remove the tubular segment 21 from the prosthesis 52 and expose the proximal end 56 of the prosthesis 52 and the reverse distal taper 72 of the enlarged body 22. Several non-limiting examples of using the intermediate handle 12 to facilitate proximal longitudinal movement of the inner cannula 26, thereby simultaneously pushing the tip body segment 20 and the tubular segment 21 proximally. During removal of the tubular segment 21 from the prosthesis 52 over about the enlarged body 22, longitudinal movement of the enlarged body 22 can be inhibited because the enlarged body 22, being indirectly coupled to the pusher 30 and thus the handle 10 via the concentric cannula 34, can be held in place. During the movement of the tubular segment 21 over the enlarged body 22 along the predetermined distance D, the positioning member 40 begins being removed from the receiving channel 46 and can begin its deployment, including at least partially flaring out, within the tubular segment 21. Upon reaching the predetermined distance D, the positioning member 40 moves to its deployed configuration, as show in FIGS. 5 and 9. The positioning member 40 can be fully removed from the receiving channel 46, radially moving or flaring to a position such that the second member end 42 engages the internal axial end 25 of the tip body segment 20. To this end, the tip assembly 18 can be now inhibited from moving any farther away from the enlarged body 22 by the engagement of the tapered distal end 37 and the proximal end 39 of the enlarged body 22, and now inhibited from moving any closer toward the enlarged body 22 by the engagement of the positioning member between the enlarged body 22 and the tip body segment 20. The positioning member 40 can lock the relative position of the enlarged body assembly 35 and the tip assembly 18 by operating as a linking member to permit the transmittal of axial force between the tip assembly 18 and the enlarged body assembly 35.

Figure 3:
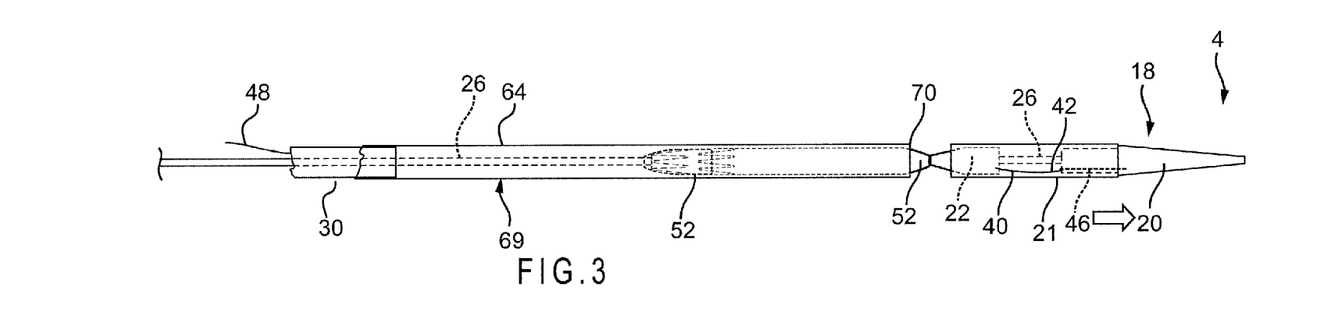
FIG. 3 is a side view of a proximal end of the prosthesis deployment system of FIG. 1, with an outer sheath in an extended position, a tip assembly being moved proximally away from a prosthesis with a portion thereof being radially expanded, and an example of a positioning member moving from a nondeployed configuration to a deployed configuration.
Figure 4:
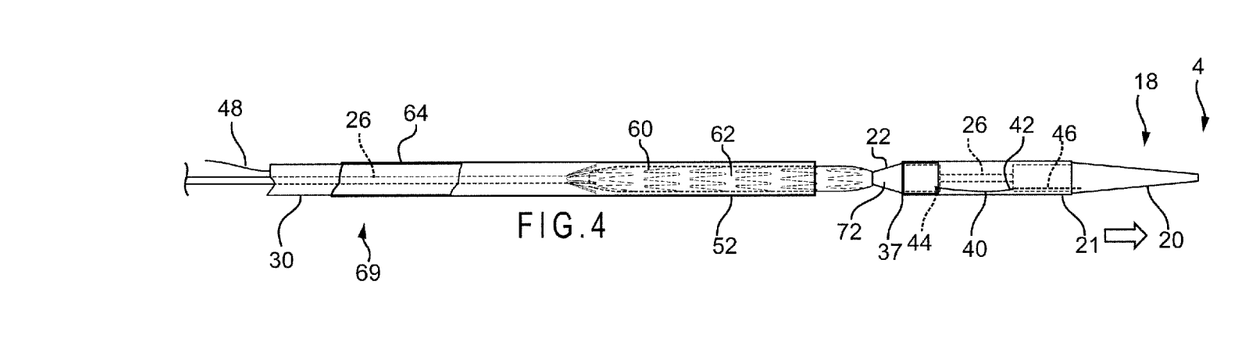
FIG. 4 is a side view of a proximal end of the prosthesis deployment system of FIG. 1, with an outer sheath partially retracted, a tip assembly moved fully away from a prosthesis with a portion thereof being radially expanded, and an example of a positioning member in a deployed configuration.
Figure 5:
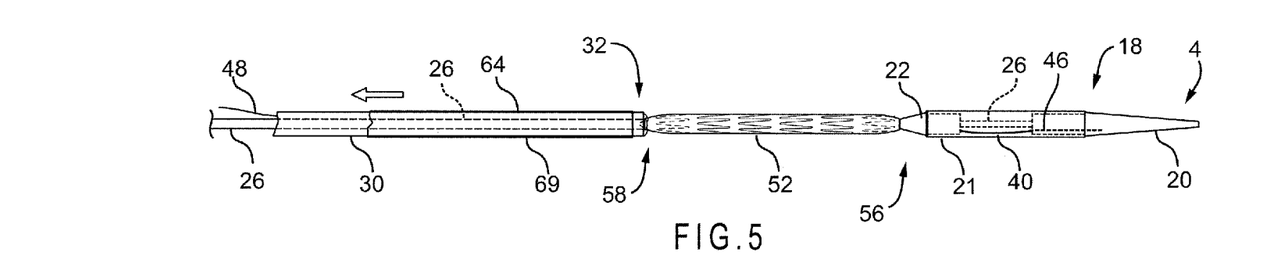
FIG. 5 is a side view of a proximal end of the prosthesis deployment system of FIG. 1, with an outer sheath being further retracted from a prosthesis with a portion thereof being radially expanded, and an example of a positioning member in a deployed configuration.

When the delivery device 2 is used to deliver the prosthesis 52 to a vessel having a branch vessel extending from a main vessel where cannulation of the branch vessel is necessary or desired, the tubular segment 21 can be only partially removed from the prosthesis 52, as shown in FIG. 3, to expose a fenestration (not shown) in the prosthesis 52 for cannulation of the branch vessel through the fenestration prior to full deployment of the prosthesis 52. This can provide a higher degree of control over the position of the prosthesis 52 and delivery device 2 during the cannulation procedure. Once cannulation of the branch vessel is complete, the tubular segment 21 can be pushed further in the proximal direction until it is fully removed from the prosthesis 52 and the reverse distal taper 72 of the enlarged body 22 can be exposed, as shown in FIGS. 4 and 9-10. Alternatively, the tubular segment 21 can be fully removed from the prosthesis 52 prior to cannulation.

The second action can be to retract the proximal end portion 69 of the outer sheath 64 in the distal direction (shown by the arrow in FIGS. 5 and 10) over the pusher 30 to remove it from the prosthesis 52 and expose the distal end 58 of the prosthesis at the proximal end 32 of the pusher 30. Several non-limiting examples of using the rearmost handle 14 to facilitate retraction of the outer sheath 64 so as to remove it from the prosthesis 52, thereby fully exposing the prosthesis 52 between its proximal and distal ends.

In one example, when the tubular segment 21 has been pushed proximally a sufficient distance to expose the proximal end 56 of the prosthesis 52 and before retracting the outer sheath 64 distally to expose the distal end 58 of the prosthesis, the user can proceed with removal of at least the proximal trigger wires (not shown) and any other diameter reducing ties that can be present at the proximal end 56 of the prosthesis (such as by manipulation of one or more trigger wire release mechanisms of the handle assembly 8 to retract the proximal trigger wires) to allow the proximal end 56 of the prosthesis to at least partially deploy radially outwardly within a vessel. Alternatively, the user can proceed with removal of at least the proximal trigger wires and any other diameter reducing ties that can be present at the proximal end 56 of the prosthesis after the tubular segment 21 has been pushed proximally a sufficient distance to expose the proximal end 56 of the prosthesis 52 and the proximal end portion 69 of the outer sheath 64 has been retracted distally to expose the distal end 58 of the prosthesis. FIG. 4 illustrates the outer sheath being partially retracted before the top assembly 18 is pushed forward.

Figure 6:
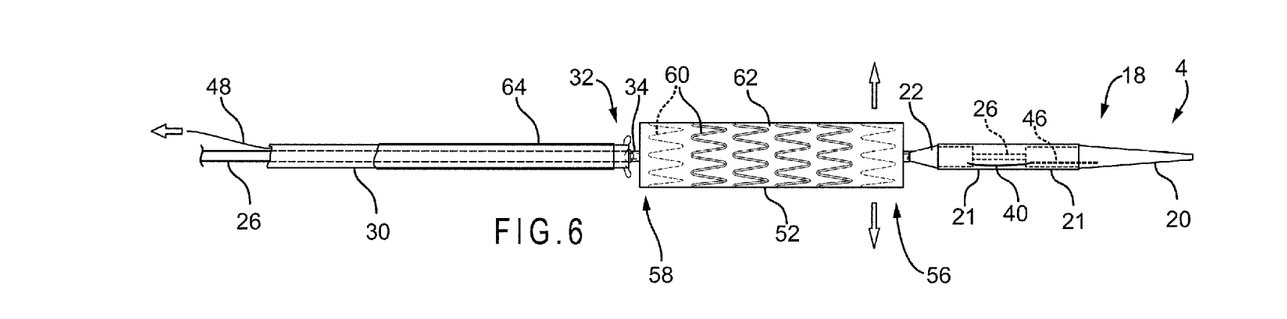
FIG. 6 is a side view of a proximal end of the prosthesis deployment system of FIG. 1, with an outer sheath fully retracted from a prosthesis, allowing the prosthesis to fully expand to a radially expanded configuration, and an example of a positioning member in a deployed configuration.

When the outer sheath 64 has been sufficiently retracted to expose the distal end 58 of the prosthesis 52 (shown in FIG. 5), the user can then retract the distal trigger wires 48 and/or any other diameter reducing ties that can be present at the distal end 58 of the prosthesis (such as by manipulation of one or more trigger wire release mechanisms of the handle assembly 8) to allow the distal end 58 of the prosthesis to at least partially deploy radially outwardly within a vessel. At this point, the prosthesis 52 can be fully deployed within the vessel, as shown in FIG. 6. In another example, the handle assembly 8 can be manipulated further to facilitate release of other components, such as, for example, the tubular segment 21 necessary to allow the prosthesis 52 to fully deploy.

Figure 7:
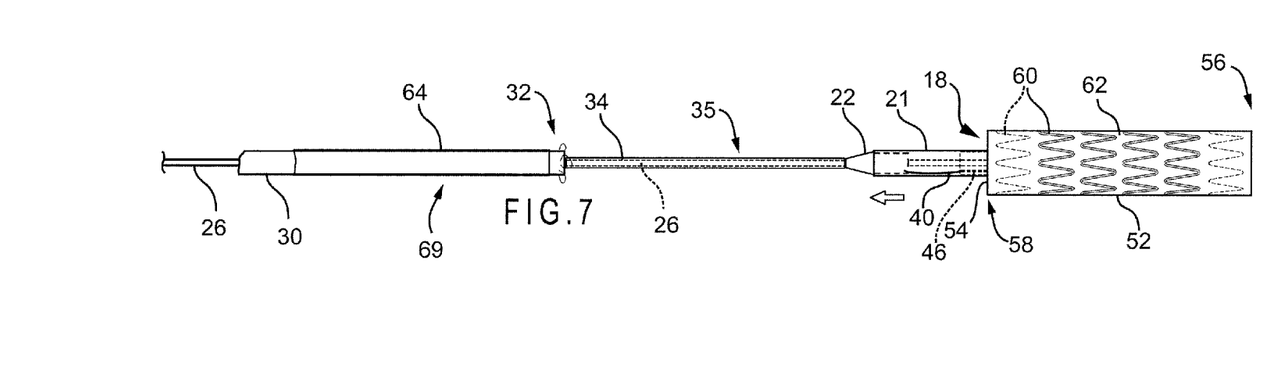
FIG. 7 is a side view of a proximal end of the prosthesis deployment system of FIG. 1, with a delivery device being withdrawn distally from a lumen of a prosthesis in a radially expanded configuration.

Once the prosthesis 52 has been fully released from the delivery device 2 and reaches its radially expanded configuration, the delivery device 2 can be removed from the patient's body. In one example, the delivery device 2 can be removed with the tubular segment 21 and the proximal end portion 69 of the outer sheath 64 in the configuration described above when the prosthesis 52 is fully deployed to its radially expanded configuration, as shown in FIGS. 6-7. In this example, since the positioning member 40 is deployed between the enlarged body 22 and the tip assembly 18 and the relative position of the enlarged body assembly 35 and the tip assembly 18 is fixed, the physician can avoid the additional step of retightening the pin vise 24 at the handle assembly 8 after being loosened to permit the inner cannula 26 to be pulled distally relative to the device 2. The axial force during pulling can be then transmitted via the inner cannula 26, tip body segment 20 and the tubular segment 21 of the tip assembly 18, the positioning member 40, the enlarged body 22 and the concentric cannula 34. The tip body segment 20 presses against the positioning member 40 and thus pushes the enlarged body 22 against the distal end 37 of the tubular segment for a tight fit and the concentric cannula 34 to allow the delivery device 2 to travel.

The positioning member 40 in the deployed configuration may fix or lock the relative position of the enlarged body 22 at the distal end 37 of the tubular segment 21 and inhibit the enlarged body 22 from substantial travel toward the tip assembly 18 within the segment lumen 21a of the tubular segment 21. As a result, edges of the distal end 37 of the tubular segment 21 may remain covered or not exposed by the engagement of the enlarged body 22, providing a smooth transition between the reverse distal taper 72 and the distal end 37. The reverse distal taper 72 of the enlarged body 22 can facilitate efficient and easy withdrawal of the delivery device 2 from the body with reduced risk of the tip assembly 18, the tubular segment 21, especially exposed edges of its distal end 37, or other portions of the delivery device 2 from snagging, catching or otherwise interfering with the deployed prosthesis 52. The delivery device 2 can then be withdrawn distally, through the lumen of the prosthesis and retracted further until the device has been safely removed from the patient's body. For a fenestrated device, the device 2 can be withdrawn distally such that its introduction end 4 can be distal to the fenestration(s) prior to deploying any connection stents that would be coupled to the fenestrations of the prosthesis.

The stent(s) 60 of the prosthesis 52 described herein is depicted as comprising one or more zig-zag stents. The stent can include shapes other than the zig-zag shape depicted. The term "stent" means any device or structure that provides or can be configured to provide rigidity, expansion force, or support to a body part, for example, a diseased, damaged, or otherwise compromised body lumen. A stent can include any suitable biocompatible material, including, but not limited to fabrics, metals, plastics, and the like. Examples of suitable materials include metals such as stainless steel and nitinol, and plastics such as polyethylene terephthalate ("PET"), polytetrafluoroethylene ("PTFE") and polyurethane. A stent can be "expandable," that is, it can be capable of being expanded to a larger-dimension configuration. A stent can expand by virtue of its own resilience (i.e., self-expanding), upon the application of an external force (i.e., balloon-expandable), or by a combination of both. In one example, a stent can have one or more self-expanding portions and one or more balloon-expandable portions. An example of a suitable self-expanding stent includes Z-STENTS®, which are available from Cook Inc., Bloomington, Ind., USA.

The term "graft" of in the graft body 62 of the prosthesis 52 describes an object, device, or structure that can be joined or that can be capable of being joined to a body part to enhance, repair, or replace a portion or a function of that body part. Grafts that can be used to repair body vessels include, for example, films, coatings, or sheets of material that are formed or adapted to conform to the body vessel that is being enhanced, repaired, or replaced. A stent can be attached to or associated with a graft to form a prosthesis or stent-graft. A graft material can include a biocompatible synthetic or biological material. Examples of suitable synthetic materials include fabrics, woven and non-woven materials, and porous and non-porous sheet materials. One exemplary synthetic graft material includes a woven polyester having a twill weave and a porosity of about 350 ml/min/cm.sup.2, and is available from VASCUTEK Ltd., Renfrewshire, Scotland, UK. Other synthetic graft materials include biocompatible materials such as polyester, polytetrafluoroethylene (PTFE), polyurethane, and the like. Examples of suitable biological materials include, for example, pericardial tissue and extracellular matrix materials such as SIS. In one example, low profile graft material is provided, which can be about one-half the thickness of the stent member.

The delivery systems described herein can need various other components in order to obtain a delivery and deployment system that is optimally suited for its intended purpose. These include and are not limited to various outer sheaths, pushers, trigger wires, stoppers, guide wires, and the like. For example, the Zenith® Thoracic Aortic Aneurysm Endovascular Graft uses a delivery system that is commercially available from Cook Inc., Bloomington, Ind., and can be suitable for delivering and deploying an aortic prosthesis in accordance with the present embodiments.

Throughout this specification, unless the context requires otherwise, the words "comprise" and "include" and variations such as "comprising" and "including" will be understood to imply the inclusion of an item or group of items, but not the exclusion of any other item or group items. While various embodiments have been described, it will be apparent to those of ordinary skill in the art that many more examples and implementations are possible within the scope of the present disclosure. Furthermore, although various indications have been given as to the scope of this present disclosure, the present disclosure is not limited to any one of these but can reside in two or more of these combined together. Accordingly, the present disclosure is not to be restricted except in light of the attached claims and their equivalents.

We claim:

1. A prosthesis deployment system, comprising:
a tip body segment coupled to an end of an inner cannula;
a tubular segment extending away from the tip body segment, the tubular segment defining a lumen between an internal axial end of the tip body segment and an edge of the tubular segment;
an enlarged body slidably disposed within the lumen of the tubular segment, the enlarged body coupled to an end of a concentric cannula that is coaxially disposed about the inner cannula; and
a positioning member at least partially disposed within the lumen of the tubular segment, having a first member end coupled to one of the enlarged body or the tip body segment, the positioning member deployable when the enlarged body is at a position corresponding to the edge of the tubular segment.

2. The system of claim 1, wherein the first member end of the positioning member is coupled to the enlarged body, wherein the positioning member is radially movable between a nondeployed configuration and a deployed configuration.

3. The system of claim 2, wherein the tip body segment includes a receiving channel sized to receive a body of the positioning member when the positioning member is in the nondeployed configuration.

4. The system of claim 2, wherein, in the deployed configuration, the positioning member is positioned within the tubular segment such that a second member end of the positioning member, opposite the first member end, is engageable with the internal axial end of the tip body segment.

5. The system of claim 1, wherein the positioning member has a spring bias to flare radially outward to a its deployed configuration.

6. The system of claim 1, wherein the positioning member comprises a wire member.

7. The system of claim 1, wherein the positioning member includes at least one undulation.

8. The system of claim 1, wherein an internal wall of the tubular segment includes a groove formed therein to receive a portion of the positioning member when in a deployed configuration.

9. The system of claim 1, wherein an internal wall of the tubular segment includes a protruding tab depending therefrom, the protruding tab engageable with a portion of the positioning member when in a deployed configuration.

10. The system of claim 1, wherein the positioning member is a first positioning member, the system including a second positioning member at least partially disposed within the lumen of the tubular segment, the second positioning member deployable when the enlarged body is at a position at the edge of the tubular segment.

11. A delivery device, comprising:
a tip cannula;
a tip body segment coupled to an end of the tip cannula, wherein a tubular segment extends away from the tip body segment, the tubular segment defining a lumen extending between an end opening of the tubular segment and an internal end of the tip body segment;
an enlarged body cannula slidably disposed about the tip cannula;
an enlarged body member coupled to an end of the enlarged body cannula, the enlarged body member slidably disposed along the lumen of the tubular segment; and
a flareable wire member at least partially disposed within the tubular segment, having a member end coupled to the enlarged body member and extending toward the tip body segment, wherein the flareable wire member is movable about the member end between a nondeployed configuration and a deployed configuration, where, in the nondeployed configuration, at least a portion of the flareable wire member is received in a channel formed in the tip body segment, and in the deployed configuration, the flareable wire member is at least partially withdrawn from the channel and moved within the tubular segment.

12. The device of claim 11, wherein the flareable wire member moves radially outward under a spring force to the deployed configuration.

13. The device of claim 12, wherein the flareable wire member includes an undulation.

14. The device of claim 11, wherein the tubular segment includes a distal end having an internal taper, wherein the distal end of the tubular segment inhibits the enlarged body from distal movement and the flareable wire member in the deployed configuration inhibits the enlarged body from proximal movement.

15. The device of claim 11, wherein the flareable wire member includes a free end, disposed opposite the member end, and, when in the deployed configuration, the free end is in contact with the internal end of the tip body segment.

16. The device of claim 11, further comprising an outer sheath extending over portions of the tip cannula and the enlarged body cannula, a proximal end portion of the outer sheath in an extended position together with the tubular segment adapted to restrain a prosthesis for delivery.

17. The device of claim 11, wherein a distal end of the tubular segment is adapted to inhibit the enlarged body member from being fully withdrawn from the tubular segment.

18. The device of claim 17, wherein the flareable wire member in the deployed configuration includes a free end engaging the internal end of the tip body segment to lock a relative position between the enlarged body member and the tip body segment.

19. A method of deployment of a prosthesis with a delivery device, including:
providing a delivery device including a tip assembly coupled to an end of an inner cannula, the tip assembly including a tip body segment and a tubular segment extending from the tip body segment, the tubular segment defining a lumen extending through an end opening of the tubular segment and terminating at an internal axial end of the tip body segment, the lumen of the tubular segment receiving a portion of a prosthesis in a radially compressed configuration, an enlarged body coupled to a concentric cannula slidably disposed about the inner cannula, and a positioning member at least partially disposed within the tubular segment of the tip assembly at a nondeployed configuration;
moving relatively the enlarged body and the tip assembly by a distance for removing the tubular segment of the tip assembly from around a portion of the prosthesis to allow the portion of the prosthesis to radially expand;

radially moving the positioning member within the tubular segment from its nondeployed configuration to a deployed configuration, the positioning member in the deployed configuration inhibiting the tip assembly from moving relatively closer to the enlarged body after moving relatively between the enlarged body and the tip assembly by the distance.

20. The method of claim 19, wherein the positioning member includes a member end coupled to the enlarged body and a free end extending toward the tip body segment, wherein when the positioning member is in its nondeployed configuration at least a portion of the positioning member is received in a port formed in the internal axial end of the tip body segment, and during the moving relatively step the positioning member is being withdrawn from the port, and wherein when the positioning member is in the deployed configuration the free end engages with the internal axial end of the tip body segment.

* * * * *

UNITED STATES PATENT AND TRADEMARK OFFICE
CERTIFICATE OF CORRECTION

PATENT NO. : 10,603,198 B2
APPLICATION NO. : 15/695382
DATED : March 31, 2020
INVENTOR(S) : Bradway et al.

Page 1 of 1

It is certified that error appears in the above-identified patent and that said Letters Patent is hereby corrected as shown below:

In the Claims

In Column 17, Claim 5, Line 41, delete "its".

Signed and Sealed this
Seventh Day of July, 2020

Andrei Iancu
*Director of the United States Patent and Trademark Office*